(12) United States Patent
Fondin et al.

(10) Patent No.: US 7,976,831 B2
(45) Date of Patent: Jul. 12, 2011

(54) METHOD FOR TREATING HAIR FIBERS

(75) Inventors: Thomas Fondin, Taverny (FR); Anne Sabbagh, Rueil Malmaison (FR)

(73) Assignee: L'Oreal S.A., Paris (FR)

( * ) Notice: Subject to any disclaimer, the term of this patent is extended or adjusted under 35 U.S.C. 154(b) by 1442 days.

(21) Appl. No.: 11/097,171

(22) Filed: Apr. 4, 2005

(65) Prior Publication Data

US 2005/0232884 A1 Oct. 20, 2005

Related U.S. Application Data

(60) Provisional application No. 60/571,920, filed on May 18, 2004.

(30) Foreign Application Priority Data

Apr. 2, 2004 (FR) ...................................... 04 50669

(51) Int. Cl.
*A61Q 5/04* (2006.01)
(52) U.S. Cl. ...................................... 424/70.51; 132/211
(58) Field of Classification Search ........................ None
See application file for complete search history.

(56) References Cited

U.S. PATENT DOCUMENTS

| | | |
|---|---|---|
| 2,047,398 A | 7/1936 | Voss et al. |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,463,264 A | 3/1949 | Graenacher et al. |
| 2,528,378 A | 10/1950 | Mannheimer |
| 2,723,248 A | 11/1955 | Wright |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,256,154 A | 6/1966 | Jenkins et al. |
| 3,472,243 A | 10/1969 | Wall et al. |
| 3,472,840 A | 10/1969 | Stone et al. |
| 3,632,559 A | 1/1972 | Matter et al. |
| 3,716,633 A | 2/1973 | Viout et al. |
| 3,810,977 A | 5/1974 | Levine et al. |
| 3,836,537 A | 9/1974 | Boerwinkle et al. |
| 3,874,870 A | 4/1975 | Green et al. |
| 3,917,817 A | 11/1975 | Vanlerberghe et al. |
| 3,929,990 A | 12/1975 | Green et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,103,145 A | 7/1978 | Oliveri |
| 4,128,631 A | 12/1978 | Lundmark et al. |
| 4,131,576 A | 12/1978 | Iovine et al. |
| 4,137,208 A | 1/1979 | Elliott |
| 4,166,894 A | 9/1979 | Schaper |
| 4,172,887 A | 10/1979 | Vanlerberghe et al. |
| 4,189,468 A | 2/1980 | Vanlerberghe et al. |
| 4,192,863 A | 3/1980 | Kondo |
| 4,197,865 A | 4/1980 | Jacquet et al. |
| 4,217,914 A | 8/1980 | Jacquet et al. |
| 4,277,581 A | 7/1981 | Vanlerberghe et al. |
| 4,282,203 A | 8/1981 | Jacquet et al. |
| 4,289,752 A | 9/1981 | Mahieu et al. |
| 4,308,878 A | 1/1982 | Silva |
| 4,348,202 A | 9/1982 | Grollier et al. |
| 4,349,532 A | 9/1982 | Vanlerberghe et al. |
| 4,367,390 A | 1/1983 | Balleys et al. |
| 4,381,919 A | 5/1983 | Jacquet et al. |
| 4,422,853 A | 12/1983 | Jacquet et al. |

(Continued)

FOREIGN PATENT DOCUMENTS

CA 714031 7/1965

(Continued)

OTHER PUBLICATIONS

INPI Search Report for FR Appl. No. 0450669, dated Dec. 3, 2004 (2 pages).

(Continued)

*Primary Examiner* — Jyothsna Venkat

(74) *Attorney, Agent, or Firm* — Finnegan, Henderson, Farabow, Garrett & Dunner, LLP

(57) ABSTRACT

The present disclosure relates to methods for treating hair fibers, wherein the hair fibers are not fixed with an oxidizing composition, comprising the following steps:
  applying to the hair fibers at least one reducing composition containing no ceramide, comprising at least one reducing agent chosen from thiols and at least one cosmetic active agent chosen from polymeric active agents;
  increasing the temperature of the hair fibers with a heating iron at a temperature of at least 60° C., wherein the temperature of the hair fibers may be increased before or after optionally rinsing the hair fibers.

8 Claims, No Drawings

U.S. PATENT DOCUMENTS

| | | | | |
|---|---|---|---|---|
| 4,452,261 A | * | 6/1984 | Bresak et al. | 132/206 |
| 4,533,714 A | | 8/1985 | Sebag et al. | |
| 4,579,732 A | | 4/1986 | Grollier et al. | |
| 4,587,321 A | | 5/1986 | Sebag et al. | |
| 4,591,610 A | | 5/1986 | Grollier | |
| 4,608,250 A | | 8/1986 | Jacquet et al. | |
| 4,749,732 A | | 6/1988 | Kohl et al. | |
| 4,761,273 A | | 8/1988 | Grollier et al. | |
| 4,777,040 A | | 10/1988 | Grollier et al. | |
| 4,795,629 A | | 1/1989 | Siuta-Mangano | |
| 4,812,307 A | | 3/1989 | Siuta-Mangano | |
| 4,832,948 A | | 5/1989 | Kondo | |
| 4,931,210 A | | 6/1990 | Takahashi et al. | |
| 4,948,579 A | | 8/1990 | Jacquet et al. | |
| 4,956,175 A | | 9/1990 | Maignan et al. | |
| 4,970,066 A | | 11/1990 | Grollier et al. | |
| 5,009,813 A | * | 4/1991 | Watanabe et al. | 510/119 |
| 5,015,767 A | | 5/1991 | Maignan et al. | |
| 5,046,516 A | | 9/1991 | Barradas | |
| 5,085,860 A | | 2/1992 | Junino et al. | |
| 5,106,612 A | | 4/1992 | Maignan et al. | |
| 5,166,355 A | | 11/1992 | Leistner et al. | |
| 5,196,189 A | | 3/1993 | Jacquet et al. | |
| 5,237,071 A | | 8/1993 | Leistner et al. | |
| 5,279,818 A | | 1/1994 | Halloran et al. | |
| 5,334,377 A | | 8/1994 | Junino et al. | |
| 5,346,691 A | | 9/1994 | Raspanti | |
| 5,449,805 A | | 9/1995 | Junino et al. | |
| 5,466,878 A | | 11/1995 | Junino et al. | |
| 5,494,058 A | | 2/1996 | Chan | |
| 5,570,708 A | * | 11/1996 | Samain | 132/205 |
| 5,583,257 A | | 12/1996 | Junino et al. | |
| 5,585,091 A | | 12/1996 | Pelzer et al. | |
| 5,643,557 A | | 7/1997 | Eteve et al. | |
| 5,695,747 A | | 12/1997 | Forestier et al. | |
| 5,708,151 A | | 1/1998 | Mockli | |
| 5,801,244 A | | 9/1998 | Raspanti | |
| 5,955,060 A | | 9/1999 | Huglin et al. | |
| 5,957,140 A | | 9/1999 | McGee | |
| 5,962,452 A | | 10/1999 | Haase et al. | |
| 5,976,512 A | | 11/1999 | Huber | |
| 5,983,903 A | | 11/1999 | Nanba et al. | |
| 6,013,249 A | | 1/2000 | Neill et al. | |
| 6,159,455 A | | 12/2000 | Habeck et al. | |
| 6,235,271 B1 | | 5/2001 | Luther et al. | |
| 2005/0025736 A1 | | 2/2005 | Jachowicz et al. | |

FOREIGN PATENT DOCUMENTS

| | | |
|---|---|---|
| CH | 353491 | 4/1961 |
| DE | 23 309 56 | 1/1974 |
| DE | 197 26 184 | 12/1998 |
| DE | 198 55 649 | 6/2000 |
| EP | 0 122 324 B1 | 1/1988 |
| EP | 0 295 780 A1 | 12/1988 |
| EP | 0 299 764 A2 | 1/1989 |
| EP | 0 354 835 B1 | 2/1990 |
| EP | 0 432 000 B1 | 6/1991 |
| EP | 0 518 772 | 6/1991 |
| EP | 0 517 104 | 12/1992 |
| EP | 0 518 773 | 12/1992 |
| EP | 0 570 838 | 11/1993 |
| EP | 0 669 323 | 8/1995 |
| EP | 0 681 828 | 11/1995 |
| EP | 0 514 282 B1 | 4/1996 |
| EP | 0 714 954 | 6/1996 |
| EP | 0 775 698 | 5/1997 |
| EP | 0 796 851 | 9/1997 |
| EP | 0 863 145 | 9/1998 |
| EP | 0 878 469 | 11/1998 |
| EP | 0 893 119 | 1/1999 |
| EP | 0 933 376 | 8/1999 |
| FR | 1 085 921 A | 2/1955 |
| FR | 1 222 944 A | 6/1960 |
| FR | 1 400 366 A | 5/1965 |
| FR | 1 492 597 A | 8/1967 |
| FR | 1 583 363 A | 10/1969 |
| FR | 2 162 025 A | 7/1973 |
| FR | 2 252 840 A1 | 6/1975 |
| FR | 2 265 781 A1 | 10/1975 |
| FR | 2 265 782 A1 | 10/1975 |
| FR | 2 270 846 A1 | 12/1975 |
| FR | 2 280 361 A2 | 2/1976 |
| FR | 2 316 271 A1 | 1/1977 |
| FR | 2 320 330 A1 | 3/1977 |
| FR | 2 350 384 A1 | 12/1977 |
| FR | 2 368 508 A2 | 5/1978 |
| FR | 2 413 907 A1 | 8/1979 |
| FR | 2 439 798 A1 | 5/1980 |
| FR | 2 505 348 A1 | 11/1982 |
| FR | 2 535 730 A1 | 5/1984 |
| FR | 2 542 997 A1 | 9/1984 |
| GB | 839 805 | 6/1960 |
| GB | 922 457 | 4/1963 |
| GB | 1 021 400 | 3/1966 |
| GB | 1 199 776 | 7/1970 |
| GB | 1 479 786 | 7/1977 |
| GB | 1 546 809 | 5/1979 |
| GB | 1 572 626 | 7/1980 |
| GB | 2 197 352 A | 5/1988 |
| GB | 2 303 549 | 2/1997 |
| JP | 2002-356408 | * 12/2002 |
| WO | WO 95/01772 | 1/1995 |
| WO | WO 95/15144 | 6/1995 |

OTHER PUBLICATIONS

European Patent Office Search Report for EP Appl. No. 05 30 0246, dated Aug. 17, 2005 (2 pages).
Derwent Patent Abstract for JP 52-154529 A.
Derwent Patent Abstract for EP 0 368 763 B1.
Derwent Patent Abstract for FR 1 530 369 A.
Derwent Patent Abstract for FR 1 564 110 A.
Derwent Patent Abstract for FR 1 580 545 A.
Derwent Patent Abstract for FR 2 336 434 A1.
Derwent Patent Abstract for FR 2 357 241 A2.
Derwent Patent Abstract for FR 2,514,640.
Derwent Patent Abstract for FR 2 679 448 A1.
Derwent Patent Abstract for JP 2000-256146 A.
Derwent Patent Abstract for JP 2001-213741 A.
Derwent Patent Abstract for LU 75370.
Office Action mailed Jan. 28, 2010, in co-pending U.S. Appl. No. 11/097,167.
Office Action mailed Jun. 29, 2010, in co-pending U.S. Appl. No. 11/097,120.
Abandoned U.S. Appl. No. 11/097,154, filed Apr. 4, 2005.
Copending U.S. Appl. No. 11/097,120, filed Apr. 4, 2005.
Copending U.S. Appl. No. 11/097,167, filed Apr. 4, 2005.
English language Abstract of JP 2002-356408, dated Dec. 13, 2002.
English language Abstract of JP 2004-002459, dated Jan. 8, 2004.
English language Abstract of JP 2004-26770, dated Jan. 29, 2004.
French Search Report for FR 04/50666, dated Dec. 6, 2004.
French Search Report for FR 04/50667, dated Nov. 30, 2004.
French Search Report for FR 04/50668, dated Mar. 31, 2005.
Office Action mailed Aug. 12, 2009, in co-pending U.S. Appl. No. 11/097,120.
Office Action mailed Jan. 6, 2009, in co-pending U.S. Appl. No. 11/097,120.
Office Action mailed Jul. 23, 2008, in co-pending U.S. Appl. No. 11/097,120.
Office Action mailed May 15, 2009, in co-pending U.S. Appl. No. 11/097,167.

* cited by examiner

METHOD FOR TREATING HAIR FIBERS

This application claims benefit of U.S. Provisional Application No. 60/571,920, filed May 18, 2004, and French Patent Application No. 04 50669, filed Apr. 2, 2004, both of which are hereby incorporated by reference.

The present disclosure relates to methods for treating hair fibers.

Several methods for obtaining the permanent reshaping of hair are known. A typical method for hair reshaping includes a series of steps, including: a first step, wherein keratin disulfide bonds (cystine) are opened with a composition containing a reducing agent; an optional rinsing step; and a third step, wherein the disulfide bonds are reformed by applying an oxidizing composition (fixing solution) to the hair after the hair has been straightened or placed under tension by a suitable means, e.g. curlers or the like, so as to give the hair a desired form. This method allows the hair to attain a waved, uncurled, backcombed, or straightened configuration.

Reducing compositions that can be used to carry out the first step of this method generally comprise thiol group-comprising compounds, such as thioglycolic acid, cysteine, cysteamine, thiolactic acid, and glycerol monothioglycolate.

In addition to the above described method, hair reshaping methods utilizing heat treatment of the hair fibers are known. For example, Patent Application No. JP 2000 256 146 describes a method to permanently reshape the hair, comprising the application of a cosmetic composition containing from 2 to 11% reducing agents and from 0.2 to 4% diammonium dithiodiglycolate. After applying the reducing composition, a heating iron is used at a temperature from 60 to 220° C. Processes in which a heating iron is used inevitably comprise a post-heating fixing step as well, which increases the treatment time.

Nevertheless, these methods are not fully satisfactory. While they are very efficient at reshaping hair, they may also cause great damage to hair fibers. Moreover, the resulting shape may be irreversible. As a result, the contrast between the parts that have been treated and the hair roots may be strongly marked as the hair regrows. In addition, if the treatment is conducted on colored hair, it very frequently causes the hair color to fade as a result of the treatment.

Thus, one aspect of the present disclosure relates to methods for treating hair fibers that compensate for the drawbacks of known methods. These methods may change hair fiber behavior while limiting the damage caused to the hair, may control hair volume, and may enhance the cosmetic benefits provided to the hair, for example in terms of softness, shine, and ease of combing, while also better preserving colored hair shades. These methods for treating hair fibers may also preserve the hair's natural aspect so as to limit the so called 'root effect', that is to say the contrast between the parts that have been treated and the roots. In addition, these methods may reduce the time required to treat the hair fibers and may give long-lasting results.

The inventors have discovered that it is possible to avoid the drawbacks of known methods by carrying out methods for treating hair fibers without a hair fixing step, comprising applying to hair fibers at least one reducing composition with no ceramide, comprising at least one reducing agent selected from thiol group-containing compounds and at least one cosmetic active agent, wherein the at least one cosmetic active agent is selected from polymeric active agents; increasing the hair fiber temperature, with a heating iron at a temperature of at least 60° C.; and optionally rinsing the hair fibers before and/or after increasing the hair fiber temperature.

Thus, one embodiment of the present disclosure relates to methods for treating hair fibers, comprising:
  applying to the hair fibers at least one reducing composition containing no ceramide, comprising at least one reducing agent chosen from thiols and at least one cosmetic active agent chosen from polymeric active agents;
  optionally rinsing the hair fibers;
  increasing the temperature of the hair fibers, with a heating iron at a temperature of at least 60° C.; and
  optionally rinsing the hair fibers;
wherein the method does not comprise applying to the hair fibers an oxidizing composition.

As used herein, the phrase "without a hair fixing step" is understood to mean without any additional application of a chemically oxidizing compositions, such as hydrogen peroxide and bromates.

In one embodiment, the at least one reducing composition does not comprise dithiodiglycolic acid or any salt thereof.

The at least one cosmetic active agent may be chosen from volatile and non-volatile, linear and cyclic silicones, and cationic, non-ionic, anionic, and amphoteric non-siliconized polymers.

Non-limiting examples of silicones that may be uses as cosmetic active agents in the methods according to the present disclosure include polydimethylsiloxanes, quaternized polyorganosiloxanes such as those described in French Patent Application No. FR 2,535,730, polyorganosiloxanes containing aminoalkyl groups modified by alkoxycarbonylalkyl substituents such as those described in U.S. Pat. No. 4,749,732, polyorganosiloxanes such as polydimethylsiloxane-polyoxyalkyl copolymer of dimethicone copolyol type, polydimethylsiloxanes with stearoxy (stearoxy dimethicone) end groups, polydimethylsiloxane-dialkylammonium acetate copolymers and polydimethyl-siloxane polyalkylbetaine copolymers as described in British Patent No. GB 2,197,352, and organo polysiloxanes modified by mercapto or mercaptoalkyl moieties such as those described in French Patent No. FR 1,530,369 and in European Patent Application No. EP 295,780.

As explained above, the cosmetic active agents may also be chosen from non-siliconized cationic polymers.

As used herein, the term "cationic polymer" is understood to mean any polymer comprising cationic moieties and/or moieties that are ionizable to cationic moieties.

Non-limiting examples of cationic polymers include polyamine, polyaminoamide, and quaternary polyammonium type-polymers, which are known products.

Among the polyamine, polyaminoamide, and quaternary polyammonium type-polymers that may be used in the at least one reducing composition used in the methods according to the present disclosure, non-limiting mention may be made of those described in French Patent Nos. FR 2,505,348 and FR 2,542,997. These polymers include:
  (1) homopolymers or copolymers derived from acrylic or methacrylic acid esters or amides;
  (2) cellulose ether derivatives comprising quaternary ammonium moieties described in French Patent No. FR 1,492,597;
  (3) cationic cellulose derivatives such as cellulose copolymers and cellulose derivatives grafted onto water-soluble quaternary ammonium monomers, described for example in U.S. Pat. No. 4,131,576, such as hydroxyalkylcelluloses, for example hydroxymethyl-, hydroxyethyl- or hydroxypropyl-celluloses, grafted for instance onto a methacryloylethyl-trimethylammonium salt, a methacrylamidopropyl-trimethylammonium salt or a dimethyldiallylammonium salt; for example polyquatemium 10 (INCI denomination);

(4) other cationic polysaccharides described, for example, in U.S. Pat. Nos. 3,589,578 and 4,031,307, such as guar gums comprising trialkylammonium cationic moieties;

(5) polymers constituted of piperazinyl moieties and linear and branched chain alkylene and hydroxyalkylene divalent groups, wherein the chains are optionally interrupted by oxygen, sulfur or nitrogen atoms or by aromatic or heterocyclic rings, as well as oxidation and/or quaternization products of these polymers. Such polymers are described, for example, in French Patent Nos. FR 2,162,025 and FR 2,280,361;

(6) water-soluble polyaminoamides, such as those described, for example, in French Patent Nos. FR 2,252,840 and FR 2,368,508;

(7) polyaminoamide derivatives, such as adipic acid/dialkylaminohydroxyalkyl dialkylene-triamine polymers, wherein the alkyl group comprises from 1 to 4 carbon atoms and is chosen from, for example, methyl, ethyl, and propyl groups, and the alkylene group comprises from 1 to 4 carbon atoms and is, for example, an ethylene group. Such polymers are described, for example, in French Patent No. FR 1,583,363.

(8) polymers resulting from the reaction of a polyalkylenepolyamine comprising two primary amine moieties and at least one secondary amine moiety, with a dicarboxylic acid chosen from diglycolic acid and saturated aliphatic dicarboxylic acids comprising from 3 to 8 carbon atoms. The molar ratio between polyalkylene-polyamine and dicarboxylic acid may range from 0.8:1 to 1.4:1. The polyaminoamide resulting from such a reaction may then be reacted with epichlorhydrine in a molar ratio of epichlorhydrine to secondary amine moiety of the polyaminoamide ranging from 0.5:1 to 1.8:1. Such polymers are described, for example, in U.S. Pat. Nos. 3,227,615 and 2,961,347;

(9) alkyldiallylamine and dialkyldiallylammonium cyclopolymers such as dimethyldiallylammonium chloride homopolymer and diallyldimethylammonium chloride and acrylamide copolymers;

(10) quaternary diammonium polymers with a number average molecular weight ranging from 1,000 to 100,000, such as those described in French Patent Nos. FR 2,320,330, 2,270,846, 2,316,271, 2,336,434, and 2,413,907 and in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020; hexadimethrine chloride (INCI denomination) is an example of this type of polymer, and it is commercially marketed by CHIMEX under the trade name MEXOMERE PO.

(11) quaternary polyammonium polymers, such as those described in European Patent Application No. EP-A-122,324;

(12) vinylpyrrolidone and vinylimidazole quaternary polymers, such as products commercially marketed under the trade names LUVIQUAT® FC 905, FC 550, and FC 370 by B.A.S.F.;

(13) polyamines, such as POLYQUART® H, commercially marketed by HENKEL and registered under the name 'POLYETHYLENE GLYCOL (15) TALLOW POLYAMINE' in the CTFA dictionary;

(14) methacryloyloxyalkyl($C_1$-$C_4$) trialkyl($C_1$-$C_4$)ammonium salt crosslinked polymers, such as those commercially marketed under the trade names SALCARE® SC 92, SALCARE® SC 95, and SALCARE® SC 96 by ALLIED COLLOIDS; and mixtures thereof.

Other cationic polymers that may be used in the at least one reducing composition used in the methods according to the present disclosure include, but are not limited to, cationic proteins and cationic protein hydrolyzates, polyalkyleneimines, for example polyethylene imines, polymers with vinyl pyridine or vinyl pyridinium units, polyamine and epichlorhydrine condensation products, quaternary polyureylenes, and chitin derivatives.

For example, the cationic polymers may be chosen from hexadimethrine chloride and dimethyldiallylammonium chloride homo or copolymers.

The at least one cosmetic active agent may also be selected from amphoteric polymers.

Amphoteric polymers that may be used in the at least one reducing composition used in the methods according to the present disclosure may be chosen from polymers comprising B and C units randomly distributed along a polymeric chain, wherein B is chosen from units derived from a monomer with at least one basic nitrogen atom and C is chosen from units derived from an acidic monomer with at least one carboxylic or sulfonic moiety, or wherein B and C are chosen from moieties derived from carboxybetaine or sulfobetaines zwitterionic monomers; B and C may also be chosen from cationic polymeric chains comprising primary, secondary, tertiary or quaternary amine moieties, wherein at least one of the amine moieties comprises a carboxylic or sulfonic moiety linked through a hydrocarbon group; B and C may also belong to a polymer chain with an ethylene-dicarboxylic unit, wherein one of the carboxylic moieties has been reacted with a polyamine comprising at least one primary or secondary amine moiety.

For example, amphoteric polymers corresponding to the meaning given above may be chosen from the following compounds:

(1) polymers resulting from the copolymerization of a monomer derived from a vinyl compound comprising a carboxylic moiety such as acrylic acid, methacrylic acid, maleic acid, and alpha-chloroacrylic acid, and of a basic monomer derived from a substituted vinyl compound comprising at least one basic atom, such as dialkylaminoalkylmethacrylates and acrylates, and dialkylaminoalkyl-methacrylamides and acrylamides. Such compounds are described, for example, in U.S. Pat. No. 3,836,537. A sodium acrylate/acrylamidopropyltrimethyl-ammonium chloride copolymer, which is commercially marketed under the trade name POLYQUAR® KE 3033 by HENKEL, is another example. The vinyl compound may also be a dialkyldiallylammonium salt such as dimethyldiallyl-ammonium chloride or diethyldiallyl-ammonium chloride. Copolymers of acrylic acid and this last monomer are commercially marketed, for example, under the trade names MERQUAT® 280, MERQUAT® 295, and MERQUAT® PLUS 3330 by CALGON.

(2) polymers comprising units derived from:
a) at least one monomer chosen from acrylamides and methacrylamides substituted on the nitrogen atom by an alkyl group,
b) at least one acidic comonomer comprising at least one reactive carboxylic moiety, and
c) at least one basic comonomer such as esters of acrylic and methacrylic acids with primary, secondary, tertiary, and quaternary amine groups, and quaternization products of dimethylaminoethyl methacrylate with dimethyl or diethyl sulfate.

Among the N-substituted acrylamides and methacrylamides that may be used according to the present disclosure, non-limiting mention may be made of moieties comprising alkyl groups which comprise from 2 to 12 carbon atoms, such as N-ethylacrylamide, N-tertiobutylacrylamide, N-tertiooctylacrylamide, N-octylacrylamide, N-decylacrylamide, N-dodecylacrylamide, and the corresponding methacrylamides.

For example, acidic comonomers may be chosen from acrylic, methacrylic, crotonic, itaconic, maleic, and fumaric acids, and alkyl monoesters comprising from 1 to 4 carbon atoms of maleic or fumaric acids or anhydrides.

Non-limiting examples of basic comonomers include aminoethyl, butylaminoethyl, N,N'-dimethylaminoethyl, and N-tertio-butylaminoethyl methacrylates.

Further non-limiting mention may be made of the copolymers with the following CTFA denomination (4th Ed, 1991): Copolymer Octylacrylamide/acrylates/butylaminoethylmethacrylate, such as products commercially marketed under the trade names AMPHOMER® and LOVOCRYL® 47 by NATIONAL STARCH.

(3) crosslinked and partially and totally alkylated polyaminoamides derived from polyaminoamides of formula (I):

$$\{CO-R_1-CO-Z\}- \qquad (I)$$

wherein:
R$_1$ is chosen from divalent groups derived from saturated dicarboxylic acids, aliphatic mono- or dicarboxylic acids with an ethylene double bond, esters of a lower alkanol comprising from 1 to 6 carbon atoms of these acids, and groups resulting from the addition of any one of these acids with a bis-primary or bis-secondary derived amine, and Z is chosen from bis-primary, and mono- and bis-secondary polyalkylene-polyamine groups, for example:
a) in molar amounts of from 60 to 100%, the group of formula (II):

$$-NH\{(CH_2)_x-NH\}_p- \qquad (II)$$

wherein x=2 and p=2 or 3, or x=3 and p=2;
wherein this group is derived from diethylene-triamine, triethylene-tetraamine or dipropylene-triamine;
b) in molar amounts of from 0 to 40%, the group of formula (II), wherein x=2 and p=1, and wherein this group is derived from ethylenediamine, and the piperazine-derived group:

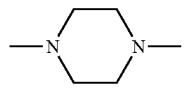

and
c) in molar amounts of from 0 to 20%, the hexamethylenediamine-derived —NH—(CH$_2$)$_6$—NH— group,
wherein the polyaminoamines may be crosslinked by addition of a difunctional crosslinking agent chosen from epihalohydrins, diepoxides, dianhydrides, and bis-unsaturated derivatives, by means of 0.025 to 0.35 moles of a crosslinking agent per polyaminoamide amine moiety, and alkylated with alkylating agents chosen from acrylic acid, chloracetic acid, alkane-sultone, and salts thereof.

For example, R$_1$ may be chosen from carboxylic or dicarboxylic acids comprising from 6 to 10 carbon atoms, such as adipic, 2,2,4-trimethyladipic, 2,4,4-trimethyladipic, and terephthalic acids, and ethylene double bond acids such as acrylic, methacrylic, and itaconic acids.

Non-limiting examples of alkane-sultones that may be used to carry out the alkylation process include propane- or butane-sultone. For example, salts of the alkylating agents may be chosen from sodium and potassium salts.

(4) zwitterionic unit-comprising polymers of formula (III):

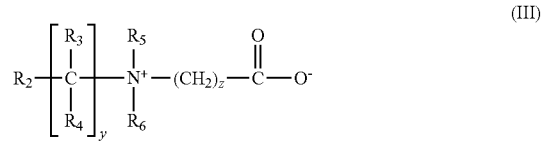

wherein:
R$_2$ is chosen from unsaturated polymerizable moieties such as acrylate, methacrylate, acrylamide, and methacrylamide moieties;

y and z, which may be identical or different, are chosen from each integers from 1 to 3, R$_3$ and R$_4$, which may be identical or different, are chosen from hydrogen atoms, and methyl, ethyl, and propyl moieties, and R$_5$ and R$_6$, which may be identical or different, are chosen from hydrogen atoms and alkyl groups, with the proviso that the carbon atom sum for R$_5$ and R$_6$ does not exceed 10.

Polymers comprising such units may also comprise units derived from non-zwitterionic monomers such as dimethyl- and diethylaminoethyl acrylate and methacrylate, alkyl acrylates and methacrylates, acrylamides and methacrylamides, and vinyl acetate.

Methyl methacrylate and methyl dimethyl-carboxymethylammonio-ethylmethacrylate copolymer are non-limiting examples of such polymers, such as the product commercially marketed under the trade name DIAFORMER® Z301 by SANDOZ.

(5) chitosan-derived polymers comprising monomer units of formulae (IV), (V), and (VI):

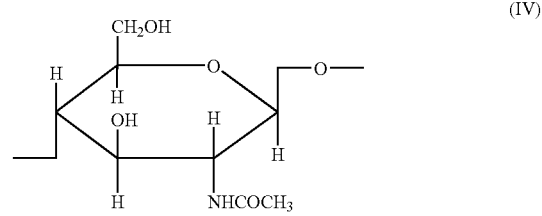

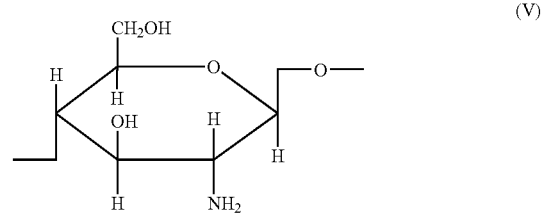

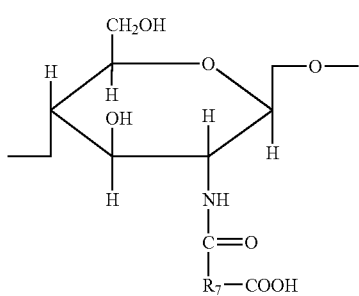

(VI)

wherein unit (IV) may be present an amount ranging from 0% to 30%, unit (V) may be present in an amount ranging from 5% to 50%, and unit (VI) may be present in an amount ranging from 30% to 90%, and wherein $R_7$ in unit (VI) may be chosen from groups of formula (VII):

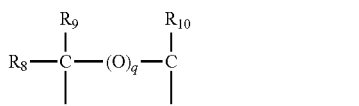

(VII)

wherein:
if q=0, $R_8$, $R_9$, and $R_{10}$, which may be identical or different, are chosen from hydrogen; methyl, hydroxyl, acetoxy, and amino radicals; monoalkylamine and dialkylamine radicals, optionally interrupted by at least one nitrogen atom and/or optionally substituted by at least one group chosen from amine, hydroxyl, carboxyl, alkylthio, and sulfone groups; and alkylthio radicals, wherein the alkyl group comprises an amine radical, with the proviso that when one of $R_8$, $R_9$, and $R_{10}$ is an alkylthio radical, at least one of the other groups is hydrogen; and
if q=1, $R_8$, $R_9$, and $R_{10}$ are hydrogen; and the salts formed by these compounds with bases or acids.

(6) chitosan N-carboxyalkylation-derived polymers such as N-carboxymethyl-chitosan and N-carboxybutyl-chitosan, such as those commercially marketed under the trade name EVALSAN® by JAN DEKKER.

(7) polymers of formula (VIII), described, for example, in French Patent No. FR 1,400,366:

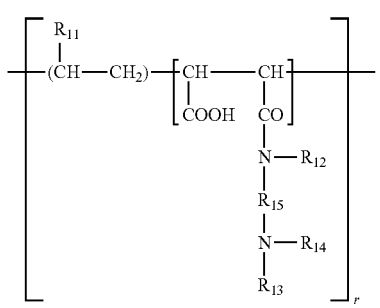

(VIII)

wherein
$R_{11}$ is chosen from hydrogen atoms, $CH_3O$, $CH_3CH_2O$, and phenyl groups;

$R_{12}$ is chosen from hydrogen atoms and lower alkyl groups such as methyl and ethyl;

$R_{13}$ is chosen from hydrogen atoms and lower alkyl groups such as methyl and ethyl; and $R_{14}$ is chosen from lower alkyl groups such as methyl and ethyl, and groups of formula $-R_{15}-N(R_{13})_2$, wherein $R_{15}$ is chosen from $-CH_2-CH_2-$, $-CH_2-CH_2-CH_2-$, and $-CH_2-CH(CH_3)-$ moieties, and $R_{13}$ has the above meaning, as well as higher homologues of these groups comprising up to 6 carbon atoms.

(8) amphoteric polymers of -D-X-D-X— type selected from:

a) polymers resulting from the reaction of chloracetic acid or sodium chloracetate with compounds comprising at least one unit of formula (IX):

-D-X-D-X-D- (IX)

wherein:
-D- is the group:

and

X is chosen from E or E', wherein E or E', which may be identical or different, are divalent groups chosen from linear and branched alkylene groups comprising up to 7 carbon atoms in the main chain, optionally substituted with hydroxyl moieties, and optionally comprising oxygen, nitrogen or sulfur atoms, and from 1 to 3 aromatic and/or heterocyclic rings, wherein the oxygen, nitrogen, and sulfur atoms may be present as ether, thioether, sulfoxide, sulfone, sulfonium, alkylamine, alcenylamine, hydroxyl, benzylamine, amine oxide, quaternary ammonium, amide, imide, alcohol, ester, and/or urethane moieties.

b) polymers of formula:

-D-X-D-X— (X)

wherein:
D is the group:

and

X is chosen from E and E", with the proviso that at least one X is E", wherein E has the above meaning and E" is a divalent group chosen from linear and branched alkylene groups comprising up to 7 carbon atoms in the main chain, optionally substituted with at least one hydroxyl group, and comprising at least one nitrogen atom, wherein the nitrogen atom is substituted with an entity chosen from alkyl groups optionally interrupted by an oxygen atom and comprising at least one carboxyl functionality or at least one hydroxyl functionality and betainized upon reaction with chloracetic acid or soda chloracetate.

(9) ($C_1$-$C_5$)alkylvinylether/maleic anhydride copolymers partially modified by semi-amidification with an N,N-dialkylaminoalkylamine, such as N,N-dimethylaminopropyl-amine, or by semi-esterification with a N,N-dialkanolamine. These copolymers may also comprise other vinyl comonomers such as vinylcaprolactame.

The at least one cosmetic active agent may also be selected from anionic polymers.

Polymers comprising groups derived from carboxylic, sulfonic or phosphoric acids and having a number molecular weight ranging from 500 to 5,000,000 are non-limiting examples of anionic polymers that may be used in the at least one reducing composition used in the methods according to the present disclosure.

Carboxylic moieties may be chosen from monoacidic and diacidic unsaturated carboxylic monomers, such as those of formula (XI):

wherein:
n is an integer from 0 to 10,
A is a methylene moiety, optionally linked to the carbon atom of the unsaturated moiety or to the adjacent methylene moiety when n is more than 1, through a heteroatom such as oxygen and sulfur,
$R_{16}$ is chosen from hydrogen, and phenyl and benzyl moieties,
$R_{17}$ is chosen from hydrogen, lower alkyl moieties, and carboxyl moieties,
$R_{18}$ is chosen from hydrogen, lower alkyl moieties, and —$CH_2$—COOH, phenyl, and benzyl moieties.

For example, in formula (XI), lower alkyl moieties may comprise from 1 to 4 carbon atoms and may be, for instance, methyl and ethyl moieties.

Non-limiting examples of anionic polymers with carboxylic moieties that may be used in the at least one reducing composition used in the methods according to the present disclosure include:
A) acrylic and methacrylic homo- and copolymers, and salts thereof, for example products commercially marketed under the trade names VERSICOL® E or K by ALLIED COLLOID, ULTRAHOLD® by BASF, acrylic acid and acrylamide copolymers sold in their sodium salt form under the trade names RETEN® 421, 423 or 425 by HERCULES, and polyhydroxycarboxylic acids sodium salts.
B) acrylic and methacrylic acid copolymers with a monoethylene monomer, such as ethylene, styrene, and vinyl esters, acrylic and methacrylic acid esters, optionally grafted onto a polyalkyleneglycol such as polyethyleneglycol, and optionally crosslinked. Such polymers are described, for example, in French Patent No. FR 1,222,944 and German Patent Application No. 2,330,956. Copolymers of this type may comprise in their chain an acrylamide unit, optionally N-alkylated and/or hydroxyalkylated, such as those described in Luxemburgian Patent Application Nos. 75,370 and 75,371, and such as those marketed under the trade name QUADRAMER® by AMERICAN CYANAMID. Acrylic acid and $C_1$-$C_4$ alkyl methacrylate copolymers, and methacrylic acid and ethyl acrylate copolymers, commercially marketed under the trade name LUVIMER® MAEX by BASF, are further non-limiting examples.
C) crotonic acid-derived copolymers, such as those comprising vinyl acetate or vinyl propionate units in their chain and optionally other monomers such as allyl and methallyl esters; vinylethers and vinylesters of a linear or branched, hydrocarbon long chain, saturated carboxylic acid, such as those comprising at least 5 carbon atoms, these polymers being optionally grafted and crosslinked; and vinyl, allyl, and methallyl esters of an α or β-cyclic carboxylic acid. Such polymers are described, inter alia, in French Patent Nos. FR 1,222,944, FR 1,580,545, FR 2,265,782, FR 2,265,781, FR 1,564,110, and FR 2,439,798. Resins 28-29-30, 26-13-14 and 28-13-10 sold by NATIONAL STARCH are non-limiting examples of commercially available products belonging to this class.
D) polymers derived from maleic, fumaric, or itaconic acids or anhydrides with vinyl esters, vinyl ethers, vinyl halogenides, phenylvinylic derivatives, acrylic acid, and esters thereof. These polymers may be esterified. Such polymers are described, for example, in U.S. Pat. Nos. 2,047,398, 2,723,248, 2,102,113, and in British Patent No. GB 839,805. Non-limiting examples include polymers commercially marketed under the trade names GANTREZ® AN or ES by ISP.

Polymers also belonging to this class include copolymers of maleic, citraconic, or itaconic anhydride and of an allylic or methallylic ester, optionally comprising an acrylamide or methacrylamide moiety, an α-olefin, acrylic or methacrylic esters, acrylic or methacrylic acids or vinylpyrrolidone in their chain, wherein the anhydride functionalities may be monoesterified or monoamidified. These polymers are described, for example, in French Patent Nos. FR 2,350,384 and FR 2,357,241.
E) Polyacrylamides comprising carboxylate moieties.

As explained above, anionic polymers may also be polymers from sulfonic acid-derived groups.

Non-limiting examples of polymers comprising sulfone moieties include those comprising vinylsulfone, styrene-sulfone, naphtalene-sulfone, and acrylamido-alkylsulfone units.

For example, these polymers may be selected from:
polyvinylsulfonic acid salts having a molecular weight ranging from about 1,000 to 100,000, and copolymers with an unsaturated comonomer such as acrylic and methacrylic acids, and esters thereof, acrylamide and derivatives thereof, vinyl ethers, and vinylpyrrolidone;
polystyrene-sulfonic acid salts, for example sodium salts with a molecular weight of about 500,000 and of about 100,000, respectively sold under the trade names FLEXAN® 500 and FLEXAN® 130 by National Starch. These compounds are described, for example, in French Patent No. FR 2,198,719;
polyacrylamide-sulfonic acid salts, such as those mentioned in U.S. Pat. No. 4,128,631, for example polyacrylamidoethylpropane-sulfonic acid, which is commercially marketed under the trade name COSMEDIA POLYMER® HSP 1180 by Henkel.

The at least one cosmetic active agent may also be selected from non-ionic polymers.

For example, the non-ionic polymers suitable for use in the present disclosure are not derived from aminoacids.

Non-limiting examples of non-ionic polymers that may be used in the at least one reducing composition used in the methods according to the present disclosure include:
vinylpyrrolidone homopolymers;
vinylpyrrolidone and vinyl acetate copolymers;
polyalkyloxazolines, such as polyethyloxazolines commercially marketed by DOW CHEMICAL under the trade names PEOX® 50 000, PEOX® 200 000 and PEOX® 500 000;

vinyl acetate homopolymers, such as the product sold under the trade name APPRETAN® EM by HOECHST and the product sold under the trade name RHODO-PAS® A 012 by RHONE POULENC;

vinyl acetate and acrylic ester copolymers, such as the product sold under the trade name RHODOPAS® AD 310 by RHONE POULENC;

vinyl acetate and ethylene copolymers, such as the product sold under the trade name APPRETAN® TV by HOECHST;

vinyl acetate and maleic ester copolymers, for example dibutyl maleate, such as the product sold under the trade name APPRETAN® MB EXTRA by HOECHST;

polyethylene and maleic anhydride copolymers;

alkyl acrylate homopolymers and alkyl methacrylate homopolymers, such as the product sold under the trade name MICROPEARL® RQ 750 by MATSUMOTO and the product sold under the trade name LUHYDRAN® A 848 S by BASF;

acrylic ester copolymers, such as alkyl acrylate and alkyl methacrylate copolymers, for example the products sold by ROHM & HAAS under the trade names PRIMAL® AC-261 K and EUDRAGIT® NE 30 D, by BASF under the trade names ACRONAL® 601, LUHYDRAN® LR 8833 and 8845, and by HOECHST under the trade names APPRETAN® N 9213 and N921 2;

copolymers of acrylonitrile and of a non-ionic monomer selected, for example, from butadiene and alkyl (meth)acrylates; non-limiting examples include the products available under the trade names NIPOL® LX 531 8 by NIPPON ZEON and those sold under the trade name CJ 0601 8 by ROHM & HAAS;

alkyl acetate and urethane copolymers, such as the product 8538-33 sold by NATIONAL STARCH;

polyamides, such as the product ESTAPOR® LO 11 marketed by RHONE POULENC;

non-ionic guar gums, which can be chemically modified or not modified.

Non-limiting examples of non-modified non-ionic guar gums include the products commercially marketed under the trade names VIDOGUM® GH 175 by UNIPECTINE and under the trade name JAGUAR® C by MEYHALL.

The modified non-ionic guar gums that may be used in the reducing compositions used in the methods according to the present disclosure may be modified, for example, by $C_1$-$C_6$ hydroxyalkyl moieties. Hydroxymethyl, hydroxyethyl, hydroxypropyl, and hydroxybutyl are non-limiting examples of suitable moieties.

These guar gums are well known in the art and may be prepared, for example, by reacting corresponding alkene oxides, such as propylene oxides, with the guar gum so as to obtain a guar gum modified by hydroxypropyl moieties.

Such non-ionic guar gums optionally modified by hydroxyalkyl moieties are sold, for example, under the trade names JAGUAR® HP8, JAGUAR® HP60 and JAGUAR® HP120, JAGUAR® DC 293 and JAGUAR® HP 105 by MEYHALL, and under the trade name GALACTASOL® 4H₄FD2 by AQUALON.

Further non-limiting examples of polymers that may be used in the at least one reducing composition used in the methods according to the present disclosure include anionic, cationic, non-ionic, and amphoteric polyurethanes.

Still further non-limiting examples of polymers that may be used in the at least one reducing composition used in the methods according to the present disclosure include polymers comprising at least one $C_{10}$-$C_{30}$ fatty chain in their structure, which are frequently referred to as associative polymers.

The at least one cosmetic active agent may be present in an amount ranging from 0.1% to 30%, for example from 0.5% to 10%, by weight, relative to the total weight of the at least one reducing composition.

As explained above, the at least one reducing composition used in the methods according to the present disclosure comprises at least one reducing agent selected from thiols, optionally used under salt form.

For example, the thiols used as reducing agents in the at least one reducing composition are chosen from cysteine and derivatives thereof, i.e. N-acetylcysteine, cysteamine, and derivatives thereof, for instance $C_1$-$C_4$ acylated derivatives such as N-acetyl cysteamine and N-propionyl cysteamine, and thiolactic acid and esters thereof, such as glycerol monothiolactate, thioglycolic acid and esters thereof, such as glycerol monothioglycolate, and thioglycerol and salts thereof.

Non-limiting examples of thiols that may be used in the reducing compositions used in the methods according to the present disclosure include sugar N-mercapto-alkyl amides such as N-(mercapto-2-ethyl)gluconamide, β-mercaptopropionic acid and derivatives thereof, thiomalic acid, pantheteine, N-(mercaptoalkyl)-ω-hydroxyalkyl amides such as those described in European Patent Application No. EP-A-354,835 and N-mono- or N,N-dialkylmercapto 4-butyramides such as those described in European Patent Application No. EP-A-368,763, aminomercaptoalkyl amides such as those described in European Patent Application EP-A-432,000 and alkylaminomercaptoalkyl amides such as those described in European Patent Application No. EP-A-514,282, and mixtures of hydroxy-2-propyl thioglycolate (⅔) and hydroxy-2 methyl-1 ethyl thioglycolate (67/33) as described in French Patent Application No. FR-A-2,679,448.

The at least one reducing agent may be present in an amount ranging from 0.1% to 30%, for example from 0.5% to 20%, such as from 1% to 10% by weight, relative to the total weight of the at least one reducing composition.

In one embodiment, the at least one reducing agent is present in an amount of less than 5% by weight, relative to the total weight of the at least one reducing composition.

The pH of the reducing compositions may range from 2 to 13, for example from 6 to 10, and may be, for instance, less than or equal to 9.

Composition pH may be adjusted by means of at least one alkaline agent, such as ammonia, organic amines such as monoethanolamine, diethanolamine, triethanolamine, 1,3-propanediamine, and 2-amino-2-methyl-1-propanol, alkaline and ammonium carbonate and bicarbonate, organic carbonate such as guanidine carbonate, and alkaline hydroxide, or by means of at least one acidifying agent such as hydrochloric acid, acetic acid, lactic acid, oxalic acid, and boric acid.

The at least one reducing composition may comprise at least one cosmetically acceptable solvent, selected, for example, from water, $C_1$-$C_6$ alcohols, for instance alkanols such as ethanol, propanol, and isopropanol, polyhydric alcohols, such as glycerol, propyleneglycol, and pentanediol, benzyl alcohol, polyol ethers, $C_2$-$C_6$ esters, N-methylpyrrolidone (NMP), and $C_3$-$C_6$ ketones.

The at least one reducing composition used in the methods according to the present disclosure may be in the form of an optionally thickened lotion, of a cream, of a gel, and of a foam.

Applying the at least one reducing composition as defined above is the first step of the methods according to the present disclosure.

For example, the reducing composition may be applied to wet and clean hair fibers.

Once the reducing composition has been applied, it can be left on, for example, for a period of time ranging from 5 to 60 minutes, such as from 5 to 30 minutes, with the hair optionally being heated/dried, for example, being placed under a drying helmet.

As explained above, the methods according to the present disclosure comprise, following the step in which the reducing composition is applied to the hair, an optional rinsing step, and then a step in which the hair fiber temperature is increased, with a heating iron at a temperature of at least 60° C.

As used herein, the term "iron" is understood to mean a heating device that functions by contacting the hair fibers.

The end of the iron, which comes into contact with the hair, may have various forms. For example, it may have a plane surface, which defines a so-called flat iron. It may also have a rounded surface, which then defines a round iron.

The iron may be applied by successive separated touches lasting about a few seconds or by gradually moving or sliding along hair locks.

Non-limiting examples of irons that may be used according to the present disclosure include all types of flat or round irons, such as those described in U.S. Pat. Nos. 4,103,145, 4,308,878, 5,983,903, 5,957,140, 5,494,058, and 5,046,516.

For example, the hair fiber temperature may be increased to a temperature ranging from 60° C. to 250° C., such as from 120° C. to 220° C.

In one embodiment, hair fibers are not rinsed before their temperature is increased.

The methods according to the present disclosure may further comprise a step wherein the hair fibers are partially pre-dried before their temperature is increased, so as to prevent the development of any substantial steam that might burn the hands of the hair stylist and the scalp of the user. This pre-drying step may be done, for example, by using a hair drier or a hood, or by allowing the hair to dry naturally.

The methods according to the present disclosure may be used to durably change the hair shape without excessively altering the hair color and/or without excessively damaging the hair fibers.

The present disclosure may be understood more clearly with the aid of the non-limiting examples that follow, which constitute various embodiments of the compositions according to the disclosure. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

EXAMPLES

The methods for treating hair fibers according to the present disclosure were carried out using a reducing composition.

The reducing compositions that were tested were as follows:

Reducing Composition 1

| L-Cysteine | 1.4 g |
| MEXOMERE PO | 2.5 g |
| 2-amino-2-methyl-1-propanol | qs pH 9.5 |
| Demineralized water | qs 100 g |

Reducing Composition 2

| Thioglycolic acid | 1.1 g |
| MEXOMERE PO | 2.5 g |
| 2-amino-2-methyl-1-propanol | qs pH 9.5 |
| Demineralized water | qs 100 g |

Reducing Composition 3

| L-Cysteine | 1.4 g |
| Thioglycolic acid | 0.3 g |
| MEXOMERE PO | 2.5 g |
| 2-amino-2-methyl-1-propanol | qs pH 9.5 |
| Demineralized water | qs 100 g |

The tests were conducted on colored, naturally curly hair. The reducing composition was applied to the hair and left on for 5 minutes. The hair was then partially pre-dried using a hair drier before being treated using a flat iron heated to 180° C.

After treatment, the hair fibers showed a good texture, a well controlled volume, a good respect of the color, and a long term durability of the effects.

What is claimed is:

1. A method for treating hair fibers, comprising:
applying to the hair fibers at least one reducing composition containing no dithiodiglycolic acid or any salt thereof or ceramide, comprising at least one reducing agent chosen from thiols and at least one cosmetic active agent, wherein:
the at least one cosmetic active agent is hexadimethrine chloride present in an amount ranging from 0.1% to 30% by weight, relative to the total weight of the at least one reducing composition, and
the at least one thiol is present in an amount of less than 5% by weight, relative to the total weight of the at least one reducing composition;
optionally rinsing the hair fibers;
increasing the temperature of the hair fibers with a heating iron at a temperature ranging from 120° C. to 220° C.; and
optionally rinsing the hair fibers,
wherein the method does not comprise applying to the hair fibers an oxidizing composition.

2. The method according to claim 1, wherein the at least one reducing agent is chosen from cysteine and derivatives thereof, cysteamine and derivatives thereof, thiolactic acid and esters thereof, thioglycolic acid and esters thereof, and thioglycerol and salts thereof.

3. The method according to claim 1, wherein the at least one reducing composition further comprises at least one solvent chosen from water, $C_1$-$C_6$ alcohols, polyhydric alcohols, benzyl alcohol, polyol ethers, $C_2$-$C_6$ esters, N-methylpyrrolidone (NMP), and $C_3$-$C_6$ ketones.

4. The method according to claim 1, wherein the at least one reducing composition is in a form chosen from an optionally thickened lotion, a cream, a gel, and a foam.

5. The method according to claim 1, wherein the reducing composition is applied to wet and clean hair fibers.

6. The method according to claim 1, wherein the reducing composition is left on the hair fibers while the temperature of the hair fibers is increased.

7. The method according to claim 1, wherein the hair fibers are rinsed out before increasing the temperature of the hair fibers.

8. The method according to claim 1, further comprising partially pre-drying the hair fibers before increasing the temperature of the hair fibers.

\* \* \* \* \*